(12) United States Patent
Mayer et al.

(10) Patent No.: US 7,900,496 B2
(45) Date of Patent: Mar. 8, 2011

(54) METHOD AND DEVICE FOR CALIBRATION SENSORS

(75) Inventors: Felix Mayer, Stäfa (CH); Mathias Deschler, Zürich (CH); Urs Rothacher, Zürich (CH); René Hummel, Zürich (CH)

(73) Assignee: Sensirion AG, Stafa (CH)

( * ) Notice: Subject to any disclaimer, the term of this patent is extended or adjusted under 35 U.S.C. 154(b) by 179 days.

(21) Appl. No.: 11/899,659

(22) Filed: Sep. 7, 2007

(65) Prior Publication Data
US 2008/0006076 A1    Jan. 10, 2008

Related U.S. Application Data

(62) Division of application No. 11/195,467, filed on Aug. 1, 2005, now Pat. No. 7,281,405.

(30) Foreign Application Priority Data

Aug. 17, 2004   (EP) .................................. 04019445

(51) Int. Cl.
G01N 21/00   (2006.01)
(52) U.S. Cl. .......................................... 73/1.06
(58) Field of Classification Search .................. None
See application file for complete search history.

(56) References Cited

U.S. PATENT DOCUMENTS

| | | | |
|---|---|---|---|
| 3,832,882 A | 9/1974 | Schoen | |
| 4,177,667 A | 12/1979 | Rolf et al. | |
| 4,590,789 A * | 5/1986 | Kunze | 73/1.06 |
| 4,733,553 A * | 3/1988 | Folk et al. | 73/1.58 |
| 4,825,684 A | 5/1989 | Nishiguchi et al. | |
| 5,604,444 A | 2/1997 | Harwood et al. | |
| 5,659,125 A * | 8/1997 | Ernst | 73/1.03 |
| 5,804,983 A * | 9/1998 | Nakajima et al. | 324/758 |
| 5,848,122 A | 12/1998 | Kurtz | |
| 5,963,027 A | 10/1999 | Peters | |
| 6,286,363 B1 | 9/2001 | Discenzo | |
| 6,418,783 B2 | 7/2002 | Sunshine et al. | |
| 6,688,156 B2 * | 2/2004 | Dietrich et al. | 73/1.68 |
| 6,690,569 B1 | 2/2004 | Mayer et al. | |
| 6,750,522 B1 | 6/2004 | Mayer et al. | |
| 6,769,285 B2 * | 8/2004 | Schneider et al. | 73/1.06 |
| 2006/0145711 A1 * | 7/2006 | Honma | 324/754 |

FOREIGN PATENT DOCUMENTS

EP   10160597   6/1998
WO   WO 99/04276   1/1999

OTHER PUBLICATIONS

U.S. Patent Publication No. 2004/0108847 (Jun. 10, 2004).
U.S. Patent Publication No. 2004/0256959 (Dec. 2004).

* cited by examiner

*Primary Examiner* — Robert R Raevis
(74) *Attorney, Agent, or Firm* — Richard F. Jaworski; Cooper & Dunham LLP

(57) ABSTRACT

A method and device are disclosed for calibrating sensors, which sensors are arranged on semiconductor chips and are e.g. to be used for detecting a substance in a fluid. The sensors are calibrated while they are still assembled on a semiconductor wafer by exposing the wafer to a calibration fluid containing a known amount of the substance to be measured. Hence, rather than first cutting the wafer, the sensors are calibrated at an early stage. For this purpose, they are placed on a chuck below a lid. The calibration fluid with known parameters is introduced between the wafer and the lid. This allows to test and calibrate a large number of sensors quickly.

18 Claims, 1 Drawing Sheet

METHOD AND DEVICE FOR CALIBRATION SENSORS

CROSS REFERENCE TO RELATED APPLICATIONS

This is a divisional of application Ser. No. 11/195,467 filed Aug. 1, 2005 now U.S. Pat. No. 7,281,405 which claims priority from European patent application 04019445.8 filed Aug. 17, 2004.

BACKGROUND OF THE INVENTION

The invention relates to a method and device for calibrating sensors, which sensors are e.g. to be used for detecting a substance in a fluid and are integrated on semiconductor chips. In a particularly advantageous embodiment, the invention relates to the calibration of sensors measuring humidity in gases.

One known type of humidity sensors uses a layer of a humidity sensitive material arranged on a semiconductor chip, as it is described in WO 01/42776. Other types of sensors e.g. use metal oxide technologies and be adapted to measure various types of substances in gases or liquids. Typical substances that can be measured are e.g. CO, $CO_2$, $NO_x$, volatile organic compounds (VOC), in particular any type of gaseous organic compounds, and any other types of compound.

Semiconductor chips are usually manufactured in wafers, where each wafer may comprise hundreds or more chips. After manufacturing, the wafers are cut to separate the chips, the chips are placed in a suitable housing and are then calibrated by exposure to fluids of known composition, as it is e.g. described in WO 01/40784.

However, manufacturing a large number of sensors in this manner is cumbersome and expensive.

BRIEF SUMMARY OF THE INVENTION

Hence, it is a general object of the invention to provide a method and device for simplifying the above process.

Now, in order to implement these and still further objects of the invention, which will become more readily apparent as the description proceeds, the method of a first aspect of the invention comprises the steps of exposing a semiconductor wafer comprising a plurality of said sensors to a fluid with an amount of said substance and performing calibration measurements on the sensors on the wafer while said wafer is exposed to said fluid.

Accordingly, calibration measurements on the sensors are carried out while the sensors are still assembled in the wafer by exposing the wafer to a fluid with a known amount of the substance to be measured. Rather than first cutting the wafer, housing the sensors and then calibrating them, the sensors are calibrated at an early stage. This allows to calibrate a large number of sensors quickly and allows to eliminate those sensors that cannot be calibrated from the further manufacturing steps. Furthermore, it requires only a small volume of calibration fluid for calibrating a large number of sensors.

One embodiment of a suited apparatus comprises a support for receiving a semiconductor wafer with a plurality of said sensors integrated thereon, a lid arranged at a distance from said sensor for forming a gap between a surface of the wafer mounted on said support and a surface of said lid, a fluid feed for introducing fluid with an amount of said substance into said gap, and a probe for contacting said sensors while said fluid is in said gap.

This type of arrangement allows to calibrate the sensors on the wafer.

In a further aspect, the apparatus for calibrating sensors comprises a support for receiving a semiconductor wafer with a plurality of said sensors integrated thereon, a lid arranged at a distance from said sensor for forming a gap between a surface of the wafer mounted on said support and a surface of said lid, a probe for contacting said sensors while said wafer is in said gap and a cooler and/or heater for maintaining said lid and said support at given temperatures.

Hence, both the chuck and the waver are temperature controlled for generating a substantially homogeneous temperature distribution around the wafer. This type of arrangement is suited for the calibration of substance sensors as well as of temperature sensors.

The method and apparatus are advantageously used for humidity sensors. In that case, the apparatus is preferably equipped with a humidity generator for preparing a gas with a known concentration of water.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

Figure 1:
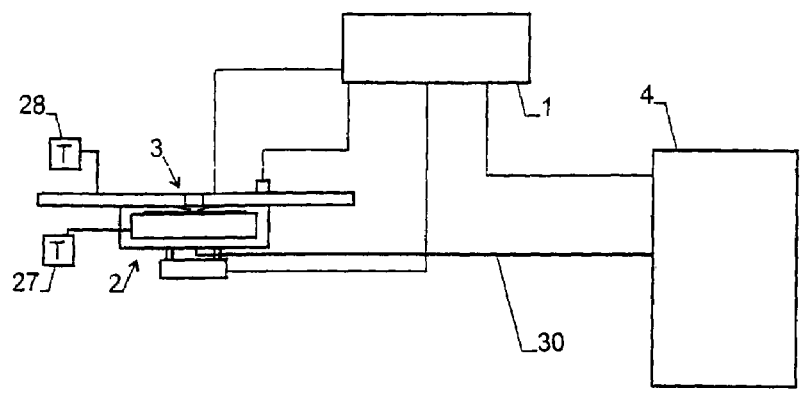
FIG. 1 is a schematic view of an apparatus for the on-wafer calibration of sensors.

Attached FIG. 1 shows the basic set-up of an apparatus for calibrating humidity sensors. In the present embodiment the sensors are humidity sensors that detect the amount of water in air or in another gas.

The apparatus comprises a control unit 1. Control unit 1 controls the operation of x-, y- and z-actuators of a testing device 2 adapted to contact each individual sensor on a wafer by means of a probe head 3. Control unit 1 further contains the circuitry and software for operating the sensors contacted by probe head 3 and for calibrating the same, e.g. by storing calibration data on a memory device integrated with each sensor. Control unit 1 also controls the operation of a humidity generator 4, which is basically a device that adds and/or removes humidity to/from a volume of gas until the same has a given level of humidity.

Figure 2:
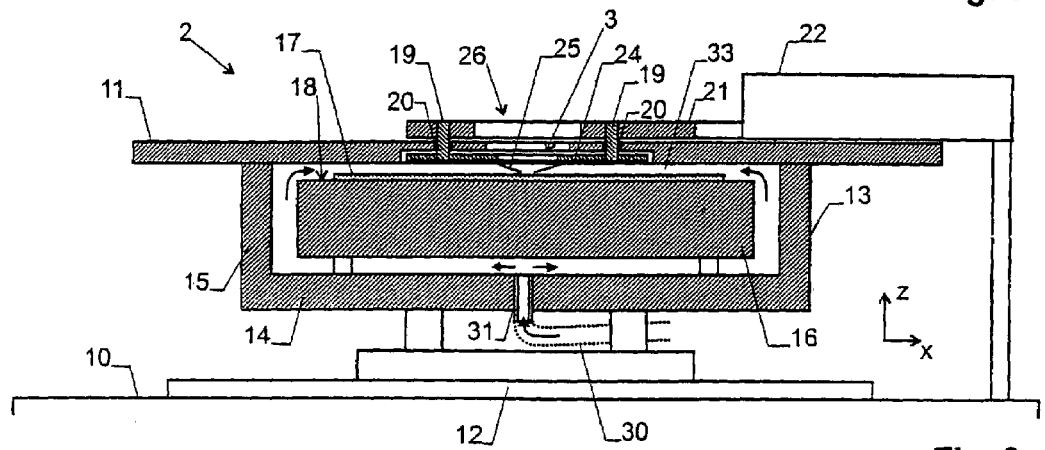
FIG. 2 is a partially sectional view of a first embodiment of part of such an apparatus.

FIG. 2 shows a more detailed view of testing device 2. Testing device 2 comprises a stationary frame or stand 10 carrying an x-y-positioning device 12.

X-y-positioning device 12 carries a housing 13 and is able to accurately position the same along the horizontal directions x and y. Direction x is illustrated by an arrow in the figure while direction y is perpendicular to the image plane.

Housing 13 has an e.g. circular bottom wall 14 and a cylindrical side wall 15. Arranged in housing 13 and substantially rigidly connected thereto is a substantially cylindrical chuck 16 acting as a support for a wafer 17. Wafer 17 contains a two-dimensional matrix of sensors that are basically ready for operation but that still need to be calibrated, cut and, where applicable, packaged. Wafer 17 rests on a flat top surface 18 of chuck 16. Chuck 16 can optionally be equipped with suction ducts (not shown) ending in top surface 18 and being used to hold wafer 17 stationary on chuck 16 as known by the person skilled in the art.

Housing 13 has an opening at its top end, which is. covered by a lid 11 at a distance of e.g. 5 mm or less from wafer 17. The top edge of housing 13 is abutting against the bottom side of lid 11 but not mechanically connected thereto, such that housing 13 can follow the motions of x-y-positioning device 12. Optionally, lid 11 and housing 13 may be mutually displaceable along the z-direction for slightly separating the two parts while x-y-positioning device 12 moves the housing.

Probe head 3 is arranged in a recess at the bottom side of lid 11 and rigidly connected to rods 19 extending through holes 20 of lid 11. Rods 19 are embedded in a positioning ring 21, which in turn is rigidly connected to a z-positioning device 22, the latter being arranged stationary on frame or stand 10. The rods 19 extending through the holes 20 hold lid 11 in x- and y-direction.

Probe head 3 comprises a carrier plate 24, with probe electrodes 25 mounted at the bottom side thereof. The probe electrodes 25 are arranged such that their tips can contact the contact pads of the sensor chips on wafer 17 as it is known to a person skilled in the art.

A central hole 26 extends through positioning ring 21, lid 11 and carrier plate 24, making it possible to view the contacting of an individual sensor chip by means of probe head 3 through a microscope.

A support cooler and/or heater 27 (see FIG. 1) is provided for heating and/or cooling chuck 16 to a given temperature, thereby substantially controlling the temperature of the wafer arranged on top of chuck 16. Support cooler and/or heater 27 may e.g. consist of a thermostat keeping a water reservoir at a given temperature and pumping water from the reservoir through ducts (not shown) in chuck 16 and/or it can comprise an electrical heater in chuck 16.

Similarly, a lid cooler and/or heater 28 is provided for heating and/or cooling lid 11. Preferably, it is set to the same temperature as support cooler and/or heater 27 and may use the same water reservoir.

For calibrating sensors with the device of FIGS. 1 and 2, a wafer comprising a plurality of sensors to be calibrated is placed on chuck 16, either manually or automatically. Humidity generator 4 is activated to generate a gas with a known humidity level. The gas may e.g. be air or nitrogen. For this purpose, humidity generator 4 can heat a dry gas to a first given temperature and add water to it until its relative humidity reaches a certain level. A pump (not shown) in humidity generator 4 then feeds the humid gas through a tube 30, from which it enters the bottom of housing 13 through an opening 31. As indicated by the arrows in FIG. 2, the gas passes through a gap between the bottom of chuck 16 and the bottom wall 14 of housing 13, then through a cylindrical gap between the vertical surfaces of chuck 16 and vertical wall 15 housing 13, to finally enter radially into the gap 33 formed between the bottom side of lid 11 and the top side of wafer 17. During its passage through these gaps, the gas is in close contact with chuck 16 and lid 11, both of which are heated to a second given temperature by means of their respective coolers and/or heaters 27, 28. For this reason, when arriving at the location of probe head 3, the gas has substantially the second given temperature and therefore a defined relative humidity.

It must be noted that the relative humidity of the gas at probe head 3 is constant even if the gas temperature is allowed to deviate from its initial value during the passage of the gas through tube 30 as long as the absolute humidity of the gas is not changed. The absolute humidity of the gas is not changed as long as its temperature does not fall below its dew point and as long as the components it passes do not absorb water in significant amounts.

Hence, because the gas is cooled or heated, in test device 2, to the known second temperature prior to or during entry into gap 33, it is not necessary to maintain its temperature accurately while it is being fed from humidity generator 4 to test device 2.

Preferably, the first given temperature used in humidity generator 4 is equal to the second given temperature in test device 2, thereby establishing the same relative humidity in gap 33 as in humidity generator 4.

The gas in gap 33 will finally leave the same through central opening 26 and the holes 20 as well as any further openings in lid 11 or housing 13. However, new gas is continuously fed from humidity generator 4 and the pressure in gap 33 is always kept slightly above ambient pressure, which prevents ambient air from entering gap 33 and affecting the humidity level of the calibration gas.

While wafer 17 is exposed to the calibration gas, the sensors on it can be calibrated by displacing housing 13 and chuck 16 and by contacting each one of them by means of the electrodes 25 of probe head 3. Calibration can consist of a calibration measurement and subsequent storage of calibration data in the sensor. Preferably, the calibration data is stored in the sensor immediately after calibrating it.

During calibration, the general functionality of each sensor can be tested as well, and non-functional sensors can be discarded after cutting wafer 17 as known to a person skilled in the art.

Depending on the nature of the humidity sensors and the desired accuracy, one or more calibration steps at different relative or absolute humidities and/or temperatures have to be carried out. A multi-step calibration can be run quickly by first carrying out the first calibration step at a first temperature and humidity for all sensors, then change the temperature and/or humidity, then run a the second calibration step for all sensors at a second temperature and humidity, etc. If only a single calibration step is required, the wafer is exposed to a given humidity and temperature and then the calibration measurements are carried out for the sensors on the wafer.

Since the volume of calibration gas in tube 30 and the gaps around chuck 16 is small, the humidity and temperature can be changed quickly, which allows to carry out a large number of calibrations in a given amount of time.

Once the calibration of the sensors on wafer 17 is complete, wafer 17 can be removed from test device 2, either manually or automatically. It then can be cut for separating the individual sensors.

Figure 3:
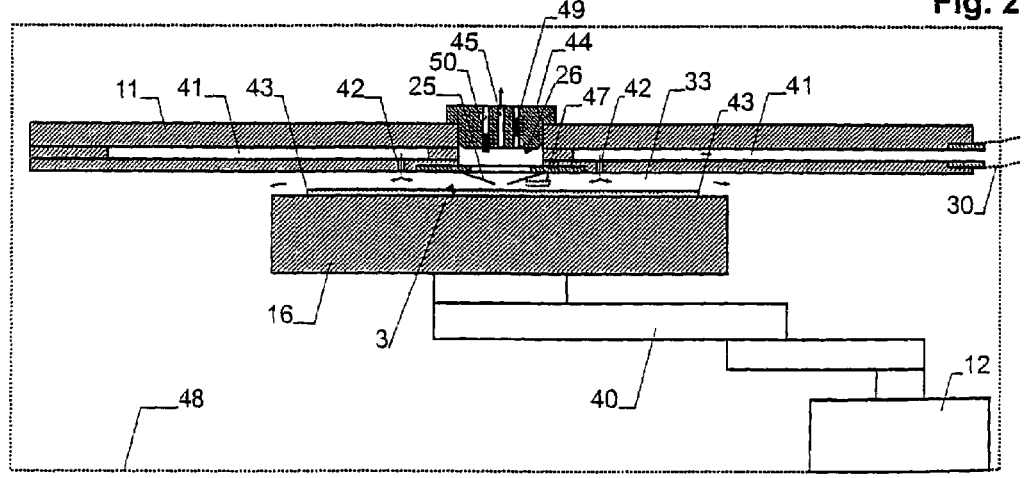
FIG. 3 is a partially sectional view of a second embodiment of part of such an apparatus.

FIG. 3 shows a second embodiment of a test device, which is particularly suited for a fully automatic calibration. In this embodiment, x-y-positioning device 12 comprises a robot arm 40 carrying chuck 16. Robot arm 40 can be used for displacing chuck 16 in respect to probe head 3 and also for bringing chuck 16 to a transfer position remote from probe head 3 for unloading and loading a wafer 17.

In contrast to the first embodiment, no housing is provided close to chuck 16. Therefore, the gas from tube 30 is introduced into a circular feed duct 41 in lid 11, from where it enters gap 33 through small openings 42 located radially between central opening 26 and a peripheral edge 43 of a centered wafer 17. From openings 42, a first part of the calibration gas flows radially outwards to exit gap 33 at its periphery, while a second part flows radially inwards to exit gap 33 through central opening 26. In order to fill the whole of gap 33 continuously and reliably with calibration gas, the amount of gas exiting through the periphery of gap 33 and the amount of gas exiting through central opening 26 should advantageously be of the same order of magnitude. To ensure this if central opening 26 has a large diameter, a plug 44 with one or more smaller openings 45 may be provided for blocking central opening 26 partially. The diameter of the openings 45 defines the ratio between the amount of gas exiting through plug 44 as compared to the amount of gas exiting radially from gap 33. Plug 44 can be removed for viewing probe head 3 through opening 26.

A further function of plug 44 is to prevent light from entering through central opening 26 during calibration because such light can lead to erroneous signals from the sensor chips.

Plug 44 can also be used in the embodiment of FIG. 2.

For contacting the individual sensors with the electrodes 25 of probe head 3, lid 11, probe head 3 or robot arm 40 of FIG. 3 can again be mounted to a suitable z-positioning device.

A calibration with the device of FIG. 3 comprises substantially the same steps as the calibration with the device of FIG. 2. Again, gas of a given absolute humidity is fed through tube 30 and enters feed duct 41, where it is brought to a known temperature. It enters gap 33 where it creates a defined environment for testing the sensors on wafer 17. Once the wafer is exposed to the calibration gas, each sensor is contacted by probe head 3. This operation can be repeated for several temperatures and/or humidities.

The diameter of the openings 42 of the device of FIG. 3 should be chosen such that the pressure drop of the incoming gas over the openings 42 is much larger than the pressure drop that the gas experiences while flowing through gap 33. This ensures that, if chuck 16 is positioned to measure a peripheral chip on wafer 17 and therefore part of the openings 42 are not directly above chuck 16, the amount of gas streaming through this part of the openings is not substantially larger than the amount of gas steaming through those openings 42 that are still above chuck 16.

In the example of FIG. 2, the calibration gas is heated and/or cooled to a given temperature primarily by chuck 16 and partially by lid 11, which therefore form a feed cooler and/or heater for adjusting a temperature of the gas prior to and during entry into gap 33. In the embodiment of FIG. 3, the role of the feed cooler and/or heater is primarily assumed by lid 11. However, depending on how the gas is introduced into gap 33, a feed cooler and/or heater separate from chuck 16 and lid 11 could be used as well.

In the previous embodiments, a humidity generator 4 has been used for preparing a gas having known, well-defined humidity. Alternatively, if the humidity of the gas is not well known in advance, it is possible to place a reference humidity sensor adjacent to the sensors to be calibrated. In such an embodiment, the reference humidity sensor can measure the humidity of the gas during the calibration process. The reference humidity sensor can e.g. be arranged on plug 44 or, as indicated under reference numeral 47 in FIG. 3, on probe head 3. If a reference humidity sensor is used, it is not necessary (even though it may be advantageous) to use a humidity generator 4 for generating the gas.

In a very simple embodiment, there is even no need to have a gap 33. Rather, the gas can be blown onto the wafer at the location of probe head 3. In that case, using a reference humidity sensor is recommended because it is more difficult to accurately control the humidity level of the gas.

In a further embodiment, the whole apparatus, of FIG. 2 or 3, including at least part of x-y-positioning device 12 and chuck 16, can be placed into a chamber containing a gas with a known humidity, e.g. in a climate controlled cabinet. In that case, again, having gap 33 is not required, nor feed duct 41. A possible location of such a chamber is indicated under reference numeral 48 in FIG. 3.

In addition or alternatively to a reference sensor 47 one or more other monitoring sensors can he located adjacent to probe head 3 for monitoring the situation at the location of calibration.

In particular, a pressure sensor 49 and/or a temperature sensor 50 can be provided, e.g. in plug 44, as indicated in FIG. 3.

Pressure sensor 49 is advantageously a differential pressure sensor for measuring the pressure difference between gap 33 and the environment—during calibration, the pressure in gap 33 should exceed the environmental pressure by a given amount in order to ensure that no environmental air can enter gap 33. Pressure sensor 49 allows to monitor this condition and to issue a warning if it is not maintained.

Temperature sensor 50 measures the temperature in gap 33 adjacent to the chips being calibrated. It allows a more accurate calibration and a monitoring of the condition of the gas.

In the above examples, the invention has been explained in the context of an advantageous application, namely the calibration of humidity sensors. As explained above, however, the invention can also be used for calibrating other types of sensors detecting a substance in a fluid. In particular, it can be used for sensors detecting substances in gases or the composition of a gas mixture, in which case humidity generator 4 is replaced by a suitable device for preparing a mixture of gases with a defined ratio. Typical substances are $CO$, $CO_2$, $NO_x$, volatile organic compounds (VOC), any type of gaseous organic compounds, and any other types of compound.

The invention could even be used for sensors adapted to measure a substance in a liquid, as long as the liquid allows the operation of probe head 3. In that case, testing device 2 is preferably arranged in a bath of the liquid.

Advantageously, when being used for calibrating sensors detecting a substance in a fluid, the apparatus of the invention should be provided with a suitable fluid feed for feeding the calibration fluid to gap 33. The fluid is advantageously fed continuously into gap 33, thereby maintaining a somewhat increased pressure therein and preventing ambient fluid from entering.

The types of apparatus described here can also be used for calibrating temperature sensors on the wafer. In particular, having a temperature controlled lid 11 and a temperature controlled support or chuck 16 allows to generate a highly homogeneous temperature distribution in gap 33, in particular if lid 11 and chuck 16 are kept at the same temperature. To calibrate temperature sensors on a wafer, the wafer is placed on chuck 16 and exposed to the temperature in gap 33. Calibration measurements can be carried out by means of probe 3.

If the apparatus is used for temperature sensor calibration, it is not necessary to provide a fluid feed as it is used for the calibration of substance sensors.

While there are shown and described presently preferred embodiments of the invention, it is to be distinctly understood that the invention is not limited thereto but may be otherwise variously embodied and practised within the scope of the following claims.

The invention claimed is:

1. An apparatus for calibrating sensors for detecting a substance in a fluid, said apparatus comprising
a support for receiving a semiconductor wafer with a plurality of said sensors integrated thereon, a lid arranged at a distance from said wafer for forming a gap between a surface of the wafer mounted on said support and a surface of said lid, a fluid feed opening into said gap for introducing fluid with an amount of said substance into said gap, and a probe for contacting said sensors while said fluid is in said gap.

2. The apparatus of claim 1 wherein said fluid is a gas and said substance is water, said apparatus further comprising a humidity generator for preparing said gas with a known amount of humidity for generating a calibration gas.

3. The apparatus of claim 1 wherein said fluid feed comprises a feed cooler and/or heater for adjusting a temperature of said fluid prior to and/or during entry into said gap.

4. The apparatus of claim 1 wherein said support comprises a support cooler and/or heater for adjusting the temperature of said support.

5. The apparatus of claim 1 wherein said lid comprises a lid cooler and/or heater for adjusting the temperature of said lid.

6. The apparatus of claim 5 wherein said support comprises a support cooler and/or heater for adjusting the temperature of said support and wherein said support cooler and/or heater and said lid cooler and/or heater are adapted to adjust the temperatures of the support and the lid to the same value.

7. The apparatus of claim 1 wherein said lid comprises a central opening for viewing said probe.

8. The apparatus of claim 7 further comprising a plug for closing said central opening.

9. The apparatus of claim 8 wherein said plug comprises one or more openings for allowing said fluid to exit from said first gap.

10. The apparatus of any of claim 1 wherein said fluid feed comprises at least one fluid duct arranged in said lid, wherein said fluid duct is opening into said gap.

11. The apparatus of claim 10 wherein said lid comprises a central opening for viewing said probe and wherein said fluid duct is opening into said gap at a radial position between said central opening, and a peripheral edge of said wafer.

12. An apparatus for calibrating sensors for detecting a substance in a fluid, said apparatus comprising:

a support for receiving a semiconductor wafer with a plurality of said sensors integrated thereon, a housing arranged around said support and having an inlet-opening for said fluid, a lid arranged at a distance from said wafer for forming a first gap between a surface of the wafer mounted on said support and a surface of said lid, a fluid feed for introducing fluid with an amount of said substance into said first gap, wherein said feed comprises a second gap between said housing and said support and wherein said second gap connects said inlet-opening with said first gap, a probe for contacting said sensors while said fluid is in said first gap, and an x- and y- positioning device for commonly displacing said housing and said support in respect to said probe for bringing individual sensors of a wafer into contact with said probe.

13. The apparatus of claim 12 further comprising a z-positioning device for displacing said probe in respect to said support and said housing.

14. The apparatus of claim 12 wherein the housing has an opening covered by said lid.

15. The apparatus of claim 12 further comprising at least one opening for allowing said fluid to exit from said first gap, wherein said feed is adapted to continuously feed said fluid to said first gap during calibration.

16. The apparatus of claim 12 wherein said support comprises a chuck having a substantially flat surface for contacting said wafer.

17. The apparatus of claim 12 further comprising a reference sensor adjacent to said probe for measuring the concentration of said substance in said fluid.

18. The apparatus of claim 12 further comprising a pressure sensor and/or a temperature sensor arranged in said first gap.

* * * * *